United States Patent [19]

Pepper

[11] Patent Number: 4,752,459

[45] Date of Patent: Jun. 21, 1988

[54] PREPARATION OF POROUS BODIES

[76] Inventor: Duncan S. Pepper, 4a, Chalmers Crescent, Edinbirgh EH9 1TR, England

[21] Appl. No.: 844,610

[22] Filed: Mar. 27, 1986

[30] Foreign Application Priority Data

Apr. 9, 1985 [GB] United Kingdom ................ 8509035
Jul. 22, 1985 [GB] United Kingdom ................ 8518449

[51] Int. Cl.$^4$ ............................................ C01B 33/12
[52] U.S. Cl. .................................. 423/338; 423/339; 423/625; 423/628; 423/636; 423/659; 502/8; 502/9; 502/439
[58] Field of Search ............... 423/338, 339, 335, 625, 423/628, 636, 659; 502/9, 8, 439

[56] References Cited

U.S. PATENT DOCUMENTS

| | | | |
|---|---|---|---|
| 3,516,935 | 6/1970 | Monforte et al. | 62/74 |
| 3,653,222 | 4/1972 | Dunn et al. | 62/74 |
| 3,681,017 | 8/1972 | Butcher et al. | 423/338 |
| 3,916,532 | 11/1975 | Jaeger et al. | 34/5 |
| 4,230,679 | 10/1980 | Mahler et al. | 423/338 |

FOREIGN PATENT DOCUMENTS

| | | |
|---|---|---|
| 1225513 | 3/1971 | United Kingdom . |
| 1322814 | 7/1973 | United Kingdom . |
| 1398117 | 6/1975 | United Kingdom . |
| 1497937 | 1/1978 | United Kingdom . |
| 1174376 | 8/1985 | U.S.S.R. .............................. 423/338 |

OTHER PUBLICATIONS

Howley "Chemical Dictionary". (9th Ed.) Van Nostrand (1977) pp. 804–805.
Aiemenz, "Principles of Colloid and Surface Chemistry" (Mariel Dikker), 1977, p. 8.

*Primary Examiner*—Asok Pal
*Attorney, Agent, or Firm*—Oblon, Fisher, Spivak, McClelland & Maier

[57] ABSTRACT

A process for the preparation of at least one porous oxide or hydroxide body comprises:
(i) adding at least one body comprising a sol of the oxide or hydroxide to a fluid freezing medium; and
(ii) raising the temperature of the solid, quenched sol so that solvent nucleation occurs, resulting in the formation of crystals of the dispersion medium, and the dispersion medium melts thereby leaving one or more porous oxide or hydroxide bodies.

18 Claims, 1 Drawing Sheet

PREPARATION OF POROUS BODIES

FIELD OF INVENTION

This invention relates to the preparation of porous oxide and hydroxide bodies; more particularly, this invention relates to the preparation of porous oxide and hydroxide particles, especially of silica, by a sol-gel conversion; and to particles so prepared.

BACKGROUND TO THE INVENTION

There are a number of different classes of sol-gel process for the preparation of porous oxide bodies known in the prior art. In one such class the dispersion medium (which is often water) is extracted from the sol particles by a medium having greater avidity therefor, resulting in their gelling. Examples of extraction media include higher anhydrous alcohols (as in the Oak Ridge process) or concentrated aqueous ammonia. The former example involves separation problems in that organic residues can only be removed from the gel particles with difficulty and in that the dispersion medium has subsequently to be separated from the extraction medium. The latter example results, in general, in a gelatinous shell forming round the remainder of the sol particle which either collapses or ruptures, both with loss of dimensional integrity, depending on the resulting osmotic stress.

In another class the dispersion medium is extracted from the sol particles by subliming the dispersion medium by freeze-drying. In U.S. Pat. No. 3,551,533 there is disclosed a process wherein a solution of a solute material, for example aluminium sulphate, is broken up into droplets which are rapidly frozen to prevent coalescence and the solvent is removed by sublimation to provide porous dried products, for example aluminium oxide, suitable for use in abrasives. Examples of refrigerating fluids disclosed include liquid nitrogen. U.S. Pat. No. 3,422,167 discloses a process for the preparation of metal oxide microspheres by dispersing a corresponding metal oxide sol into a freezing medium and subsequently dehydrating the sol by vacuum distillation, and then calcining.

This invention seeks to provide an improved process for preparing porous oxide and hydroxide bodies, for example microspheres, which is both simpler and cheaper than conventional processes and results in a cleaner product.

THE INVENTION

According to one aspect of this invention, there is provided a process for the preparation of at least one porous oxide or hydroxide body, which process comprises:

(i) adding at least one body comprising a sol of the oxide or hydroxide to a fluid freezing medium; and (ii) raising the temperature of the solid, quenched sol so that solvent nucleation occurs, resulting in the formation of crystals of the dispersion medium, and the dispersion medium melts thereby leaving one or more porous bodies.

The oxide may comprise silica or alumina; a transition metal oxide such as titania, zirconia, hafnia and iron oxide; a rare earth oxide such as ceria, samaria, europia and gadolinia; an actinide oxide such as thoria, urania, or plutonia; or a mixture thereof. The process is particularly suited to the product of porous silica bodies.

While the invention is not limited thereto, it is preferred that the sol is an aquasol. A particularly convenient silica aquasol is that marketed by Dupont under the name "LUDOX HS-40". Other grades of LUDOX colloidal silica, known as "LUDOX TM", "LUDOX AM" and "LUDOX AS" have also been used successfully. (LUDOX is a Trade Mark.)

The sol is preferably destabilised to a metastable state prior to freezing. The term metastable state is used to mean a sol with a gel time of between 1 hour and 70 days, preferably between 3 hours and 24 hours, at room temperature. De-stabilising is conveniently achieved by adding, say, an acid or a salt, resulting in lowering of the pH of the sol to in the range 4 to 9.

During the process, crystals of the dispersion medium of the sol form (nucleate) within the body or bodies after addition to the freezing medium. It is thought that nucleation may occur both during the freezing (cooling) stage and the subsequent warming stage, the timing of nucleation depending on factors including the size of the body or bodies being treated.

Various additives may also be added to the sol prior to freezing, to alter the size (and possibly also shape) of the dispersion medium crystals formed and hence pore size. Possible additives for this purpose include salts, organic solvents, low molecular weight organic molecules, polymers and solid suspensions. For example, the addition of 0.3 M NaCl (which also can conveniently be used to destabilise fresh sol) results in the production of larger pores, larger volume and narrower pore size distribution. It also protects against volume collapse during subsequent heating. The addition of glycerol similarly results in production of larger pores, but gives no protective effect against volume collapse during subsequent heating. It is thought that other additives will result in smaller sized macropores.

The fluid freezing medium is at a temperature below the freezing point of the sol (say about $-5°$ C.) and is preferably at a lower temperature, of at least $-20°$ C., for reasons of efficiency because of poor heat transfer in practice. The fluid freezing medium is preferably a liquified substance which is a gas or vapour at STP although this is not essential. The fluid freezing medium should also not enter into any unwanted chemical reaction with either the sol or the gel. Examples of suitable fluid freezing media include liquid nitrogen, liquid oxygen, liquid ammonia, a liquefied noble gas such as argon, a liquefied chlorinated hydrocarbon such as trichloroethylene or chlorofluorocarbon such as a freon, or an inert, low-boiling hydrocarbon such as hexane, dimethylbutene, isoheptane or cumene. It is also possible to use the vapour of boiling liquid nitrogen. From the standpoints of economy, inertness and ease of expulsion, liquid nitrogen is particularly preferred. The freezing medium may be either stationary or moving. For example, the surface of the medium may be vibrated to avoid drop collision. Alternatively, a flowing medium may be used.

In a preferred aspect of this invention a plurality of particles, especially microspheres, is prepared. This is suitably effected by adding the sol to the fluid freezing medium as a spray of droplets. Typically, the droplets can have a diameter from 1 micron to 1 cm, preferably 5 micron to 5 mm, especially 10 micron to 1 mm.

A spray of such droplets can be formed in known manner: for example by passing the sol through a spinning disc atomiser, a vibrating acoustically modulated nozzle, a concentric blown nozzle or a simple gravity drip feed, the latter being sufficient for large particles from 1 mm to 1 cm. When using a vibrating acoustically modulated nozzle, the drops are preferably deflected sideways by electrostatic charging to prevent drop collision. This results in the production of monosize spheres. The choice of technique depends on the size of final particle desired, on the particle size distribution tolerance, on the required mass throughput and on the throat diameter of the fluid freezing medium reservoir.

Alternatively, larger bodies may be produced. For example, the following physical forms have been fabricated:

(a) thin sheets 2 cm×2 cm×100 micron using two glass microscope slides spaced apart by appropriate thickness of glass coverslips;

(b) cylinders 2 cm long by 1 cm in diameter by moulding in low density polyethylene of similar dimensions; and (c) thin rods 1 mm in diameter by 5 cm long, by moulding in polyethylene tubing.

The glass slides can be used as a support for further handling whilst the low density polyethylene can simply be burnt off at 600° C.

The sol may be added to the freezing medium in the form of an emulsion. This is appropriate for the production of smaller particles, in the range 0.1 to 20 micron in diameter. The drops of emulsified sol may be of any convenient size, eg 2 to 5 mm in diameter, and may be of an inert fluid immiscible with aqueous sols (e.g. toluene, mineral and vegetable oils, ethyl acetate etc.) and containing low HLB detergent (e.g. Span 80) which serves readily to disperse and stabilise the small drops (e.g. 0.1 to 20 micron) of sol in the emulsion. On freezing and thawing the large drops of emulsified sol, the inert medium fluid can be drained off and/or evaporated leaving macroporous beads of a size which could not be directly sedimented in air. For example, freezing of emulsions, e.g. in liquid paraffin (mineral oil), followed by breaking of the emulsion with aqueous detergents has been found to yield particles with diameters in the range 1 to 10 micron.

One or more bodies of the solid, quenched sol is then collected, for example by sedimentation or filtration, and the temperature thereof is raised. The rate at which the temperature is raised is not critical, and conveniently is at a rate from 1000° C./min to 0.2° C./min preferably from 100° C./min to 2° C./min. Very satisfactory results can be attained by permitting the temperature of one or more of the bodies of the solid, quenched sol to rise to ambient under the autogenous thermal gradient, typically over a period from 5 minutes to 24 hours. Pressure conditions are also not critical, and these steps are conveniently carried out at atmospheric pressure.

If desired, for example to increase the strength or stability of the one or more porous oxide bodies, the or each such body may be heated to a temperature from 80° C. to 1000° C., for example from 250° C. to 850° C. Variable degrees of heating are optional for increasing the strength of the fresh bodies and reducing surface area where this is appropriate.

For low pressure or other applications where high bead strength is not important, the beads need not be dried but instead can be kept in suspension, e.g. aqueous suspension, after thawing, thus obviating the need to dry. This has advantages in reducing dust formation due to friction during handling and reduces energy costs.

It is found that bodies produced by the method of the invention have an array of macropores (in spaces left by vacating dispersion medium) all above about 500 nm in diameter, typically in the range 1000 to 10000 nm in diameter. The pattern of macropore shape, size and interconnection is fern-like as a result of solvent crystallisation. In fresh (unheated) beads, each macropore is surrounded by a plurality of micropores typically 1 to 10 nm in diameter, e.g. 3 nm in diameter, in spaces between sol particles. (If the micropores are undesirable they can be removed by heat-induced coalescence to produce mesopores of e.g. 100 nm diameter.) Thus a heirarchy of large pores leads to a smaller pore network, which is an efficient method of distribution. The resulting body thus has two discrete sizes of pores interconnected intimately, with the interpenetration of large pores and small pores being uniform throughout the body so that free access is provided throughout the structure. The potentially large difference in size between the two types of pore and the uniformity of distribution throughout the body have significant advantages when considering anchoring of molecular coatings. This structure is to be contrasted with that of conventional two zone porous bodies, for example as disclosed in U.S. Pat. No. 3904422, in which a more permeable outer shell surrounding a less permeable inner core is produced by a two step controlled etching process.

The microporous nature of the internal surface walls of the large internal cavities in bodies produced by the process of the invention provides a surface roughness and porosity which has the practical benefit of providing 3-dimensional modes of adsorption as opposed to 2-dimensional (i.e. flat surface) mode found e.g. with conventional heat treated silica. This in turn means that the effective capacity of an adsorbent will be enhanced.

For example, consider the adsorption of a flexible polymer molecule within an internal cavity. With a conventionally produced smooth surface (2-dimensional) pore, polymer molecules can only be adsorbed on the flat surface of the pore so that potential areas of overlap where crosslinking can occur are very restricted. Further, comparatively small numbers of molecules are adsorbed and there is little possibility of flexible movement. In contrast, with a combined macroporous/microporous (3-dimensional) pore produced by the process of the invention, polymer molecules can be adsorbed not only on the surface of the macropore but also on the surface of the adjacent micropores, extending transversely thereto. This greatly increases the number of molecules which can be adsorbed, the number of possible crosslinking sites and also the possibility of flexible movement. Additionally, crosslinking of the adsorbed molecules on the "3-dimensional" surface will have lower leakage, which is an advantage in extending the working life of an industrial adsorbent and also in reducing the hazards of a biomedical device.

This invention also provides a porous oxide or hydroxide body, or porous oxide or hydroxide particles, especially comprising silica, whenever prepared as herein described.

This invention further provides porous oxide or hydroxide bodies, especially comprising silica having a porosity greater than 1 ml/g, preferably having pore dimensions greater than 50 nm. Preferably, the bodies have an average particle size not greater than 5 mm, more preferably not greater than 250 micron.

The process of the invention enables porosity to be introduced with readily and easily controlled values of specific porosity (% void) and pore diameter (e.g. 3000 nm) and narrow pore size distribution, by modulating solvent crystal form. Further the invention enables production of a body of uniform predictable size and porosity in which the two parameters of size and porosity are independently variable and predictable.

The present invention thus enables provision of a process has the following advantages: vacuum sublimation (freeze drying) is unnecessary, thereby facilitating continuous and lower cost production; the raw materials are inexpensive and there is no need of energy impact in drying; there are no toxicity, handling or separating problems; the process is susceptible of ready automation and scale-up. In addition, oxide bodies of such high porosity and large pore dimension are not readily prepared by conventional processes.

The porous oxide and hydroxide bodies of this invention may be used in industrial chemistry as filter bed media, catalyst supports, metallising pastes and abrasives. Particularly important uses, especially for porous silica bodies of this invention, reside in biotechnological applications. For example, oreparative and analytical HPLC packing; industrial chromatography, for example whey sweetening and interferon production; affinity chromatography; replacement of existing filter supports for example agarose gel and plastic beads; haematological applications, for example removal of toxic materials from plasma and the extraction of therapeutic blood factors from donor plasma; and enzyme immobilisation. In this case, enzymes or other materials not adversely affected by subsequent body formation processes may be added to the sol prior to freezing. In certain cases, e.g. addition of enzymes for purification purposes, it is found that the resulting bodies have better properties as compared with formed bodies to which the relevant material has been subsequently added.

Because the process of the invention need not require the use of heat or chemical polymerising reagents and because it operates well at pH 7, the process can be used to incorporate by entrapment or microencapsulation (i.e. physical entrainment) living or dead biological cells and other materials unaffected adversely by subsequent body formation processes into the resulting porous bodies. Accordingly, the process can be used for trapping materials such as proteins e.g. enzymes, bacteria, yeasts, fungi, plant cells and even mammalian cells and other materials such as polymers in rigid porous beads for biosynthesis, conversion etc., by adding the relevant material to the sol prior to freezing. Magnetic particles may additionally or alternatively be incorporated, e.g. by including a dispersion of colloidal magnetic particles in the feedstock, it being possible for magnetic properties to be retained in the final bead product because of the possible absence of heat treatment.

Where the entrapped material is expected to be labile or have a limited shelf life when dried or kept at room temperature, the bodies need not be warmed up above a convenient (low) temperature, e.g. $-40°$ C. to $-20°$ C., until required for use. In this way, large batches of labile material can be fabricated and stored over long periods of time whilst withdrawing smaller aliquots from frozen stock at shorter intervals.

Because the process of the invention need not involve high temperatures, say above $500°$ C., silica spheres can be produced with large numbers of accessible free hydroxyl groups on the surface: such groups may be used for subsequent chemical activation and coupling to produce immobilised enzymes, e.g. in dairy byproduct processing. This feature thus eliminates the need to use costly and hazardous alkaline etching processes, for example as disclosed in U.S. Pat. No. 4384035.

Material produced by the process of the invention can also be used for adsorbing fibrinogen directly via surface hydroxyl groups, instead of using naturally ocurring diatomaceous earth for this purpose, e.g. as disclosed in U.S. Pat. No. 4381346. This naturally occurring material although slightly porous has a very small surface area (typically 0.4 to 4.0 $m^2/gm$) and is irregularly shaped so that capacity (equivalent to surface area plus hydroxyls) and flow rate (equivalent to sphericity) are both poor. Accordingly, material in accordance with the invention would perform better in this application also.

The invention will be further described, by way of example, with reference to the accompanying drawings.

IN THE DRAWINGS

DETAILED DESCRIPTION OF THE DRAWINGS

Figure 1:
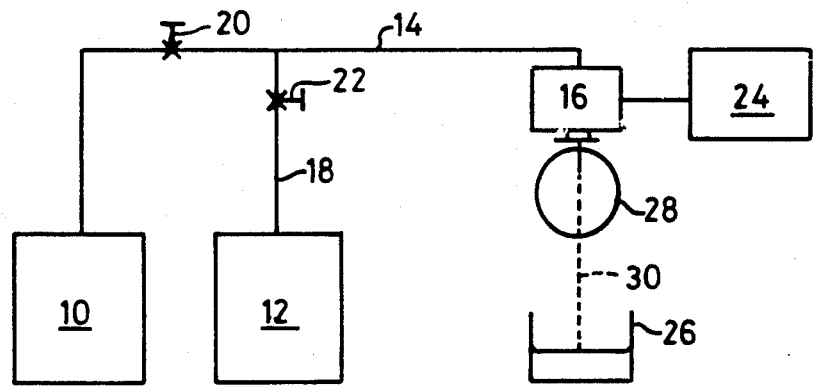
FIG. 1 is a schematic view of one embodiment of drop-forming apparatus.

Referring to the drawings, FIG. 1 illustrates apparatus for producing monodisperse drop streams. The apparatus comprises first and second pressurised liquid containers 10 and 12, containing LUDOX (Trade Mark) colloidal silica and distilled water for flushing, respectively. The pH of the colloidal silica is adjusted to an appropriate value by adding hydrochloric acid. The containers are subjected to a pressure of about 50 psi.

The first container 10 is connected by line 14 to a drop generator 16, with a side line 18 connecting container 12 to the line 14. Valves 20 and 22 are located in lines 14 and 18, respectively, for controlling flow of colloidal silica and distilled water to the drop generator 16.

The drop generator has drive electronics associated therewith, as represented at 24, and is located above a collection beaker 26 containing liquid nitrogen. A stroboscope 28 is located below the drop outlet of drop generator 16 for monitoring the drops produced thereby.

In use, with valve 20 closed valve 22 is opened permitting distilled water to flow to the drop generator. The distilled water passes a first 10 micron fibre filter (not shown) and then a second 7 micron porous stainless steel filter (not shown) and then enters a chamber in the drop generator 16. From there is passes through a nozzle of 70 micron which results in formation of a laminar jet of fluid. At the same time, an acoustic pressure wave is generated in the chamber by means of a piezo electric resonator situated in one wall of the chamber, the wave causing the velocity of the fluid stream to be modulated. The frequency of the modulation and the jet velocity are chosen so that the modulation wavelength on the jet is typically 70% of the jet circumference, with the result that the jet resolves by the action of surface tension into a stream of drops. Given a constant frequency, the drops are uniform in size. Typically with a stream velocity of 20 m/s, the rate of drop formation is in the range 60–70,000 per second, equivalent to a production rate of about 10 grams per minute.

After a start up period with flushing fluid, the first container 10 containing the acidified sol is connected to the drop generator by opening valve 20, and the second container 12 was isolated by closing valve 22. After a settling period and after adjusting the pressure to restore the jet velocity and drop size to their preferred values, the drop generator is set up for the production of silica spheres. By observing the drop stream with the stroboscope 28 at the (or a fraction of the) drop formation frequency a stable drop stream can be seen apparently frozen in space. The drop spacing viewed in this way can be normalized to control drop size. The same process can be performed automatically using drop stream sensors and a feed back system on fluid pressure.

Drops can be produced in this way covering a wide range of drop diameters (10 micron-1 mm) by varying the nozzle diameter and other parameters.

The resulting drop stream 30 flows into the liquid nitrogen in beaker 26, resulting in freezing of the sol. The solid, quenched sol particles are then collected for example by sedimentaiton or filtration, and the temperature thereof raised, resulting in production of porous silica spheres.

It is found in practice that because of the drop stream velocity the drops merged in the liquid nitrogen and that the sphere had sizes that were multiples (1, 2, 3 etc) of the drop size.

To avoid problems of drop merging it is preferred to use a process in which the surface of the liquid nitrogen is kept in motion and in which the drops and deflected laterally so that they are spread out on the liquid nitrogen surface and do not contact or merge until after freezing. This is conveniently effected using modified apparatus as illustrated schematically in FIG. 2.

Figure 2:
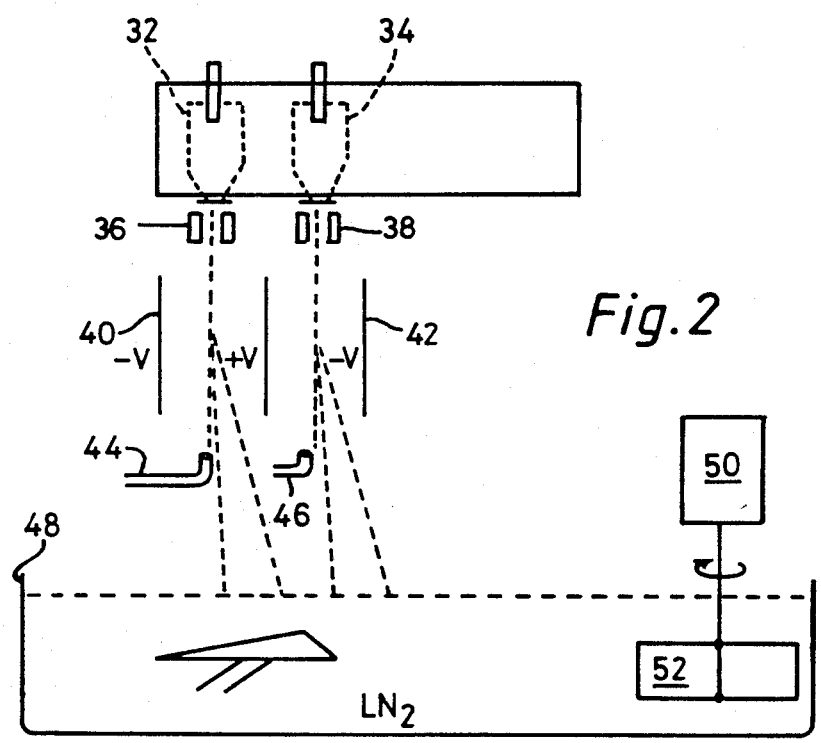
FIG. 2 is a schematic view of a further embodiment of drop-forming apparatus.

The apparatus illustrated in FIG. 2 comprises two drop generators 32 and 34 each of which has associated therewith a respective charge electrode 36, 38 and a respective deflection electrode 40, 42. Each charge electrode is subjected to a sawtooth or staircase voltage waveform which induces on each successive drop (of the group of drops generated during the period of the waveform) a different induced charge. The deflection electrodes are subjected to voltages of + or −V which induce a substantial electric field between the electrodes. This field acts on successive drops and deflects them in proportion to the induced charge and so spreads them over the receiving surface.

A respective collector 44, 46 is provided beneath each drop generator for collecting any undeflected drops.

As with the previous embodiment, a vessel 48 containing liquid nitrogen is located below the drop generators. In this case, however, a motor 50 and associated paddle 52 is provided for stiring the liquid nitrogen in the vessel and keeping the liquid in motion.

By deflecting the drops into 50-100 separate tracks and by moving the liquid nitrogen surface the drops are spread out on the surface and prevented from touching one another. On impact of each drop with the liquid nitrogen, some nitrogen gas is boiled off as the drop cools, resulting in the drop being suspended on the surface. As the drop cools and boiling stops, the resulting spheres of silica sink and are collected from time to time.

The presence of a like charge on each particle, imparted by the drop charging and deflecting apparatus also has a beneficial effect in that mutual repulsion between like charged particles is opposing the tendency of particles to fuse when touching in the pre-frozen state.

Because of this charge, it is convenient to use an earthed metal dewar vacuum chamber as the final collection vessel and to contain the liquid nitrogen, thus the final product has no charge and is more easily handled as a powder.

As will be it apparent, a large number of drop generators, may be provided, and the drops may be collected from under the liquid nitrogen surface on a moving belt, which is drained and then passes slowly through a drying oven. In this way, a continuous production orocess of macroporous monodisperse silica spheres is able to produce several kg per hour of product.

The following Example illustrates the invention.

EXAMPLE 1

20 ml of a silica aquasol (LUDOX HS-40 ex of pH 10 (higher pH gives a longer shelf life whereas lower pH gives a stronger product)) was first acidulated to a pH from 9 to 5.7. The aquasol was then charged to a spinning disc atomiser (8 cm dia, 4000 rpm) and sprayed into a reservoir of 1,000 ml of liquid nitrogen at −196° C.

When the bodies of silica aquasol impinged on the liquid nitrogen surface their intrinsic heat content caused local boiling of the nitrogen such that each body, as it was quenched to a homogeneous solid, hovered on a cushion of nitrogen which maintained its shape and integrity and permitted the use of a shallow (typically no deeper than 10 cm) reservoir. When fully frozen, the solid quenched aquasol bodies automatically sink to the base of the reservoir where they settled onto a 20 micron mesh nylon cloth 32 cm×32cm and were subsequently harvested.

The solid quenched aquasol bodies so harvested were next permitted to warm under autogenous thermal gradient by leaving overnight in open trays at room temperature. At −40° C. it was observed that water separated as ice crystals, the silica precipitating as hydrated silica gel. On attaining ambient temperature the water had drained away and the spherical bodies, which were solid and free-flowing, were heated at 40° C. for 2h, then at 100° C. for 2 h; collected; and, if desired, classified in known manner.

The spherical bodies were found to have a porosity of 2 ml/g and large pore dimensions greater than 1000 nm. They have an average particle size of 100 micron.

EXAMPLE 2

LUDOX HS-40 sol pre-adjusted to pH 8.3 was sprayed in droplet patterns from the device shown in FIG. 1 at 80 psi and 64 kHz through a 75 micron diameter nozzle and collected in liquid nitrogen. After warming up to room temperature overnight, a uniform sample of particles of 140 micron diameter was obtained with no observable aggregation or variation in size. The particles after drying in a microwave oven had a total BET surface area of 173 $m^2/g$ and a macropore diameter of 1,000 nm.

I claim:

1. A process for the preparation of at least one porous oxide or hydroxide body having a pores of a diameter greater than 500 nm, which process comprises:
   (i) adding at least one body consisting essentially of a sol of the oxide of hydroxide to a fluid freezing medium to thereby obtain a solid, quenched sol;
   (ii) recovering said solid quenched sol and raising its temperature so that solvent nucleation occurs in at least step (ii), resulting in the formation of crystals of the dispersion medium and the dispersion medium melts, and (iii) separating one or more solid porous bodies having pores of a diameter greater than 500 nm from the dispersant.

2. A process according to claim 1, wherein the oxide comprises one or more selected from the following: silica, alumina, a transition metal oxide, a rare earth oxide, and an actinide oxide.

3. A process according to claim 1, wherein the sol is an aquasol.

4. A process according to claim 1, wherein the fluid freezing medium comprises one or more selected from the following: liquid nitrogen, liquid oxygen, liquid ammonia, a liquefied noble gas, a liquefied chlorinated hydrocarbon, a liquefied chlorofluorocarbon, and an inert, low-boiling hydrocarbon.

5. A process according to claim 1, wherein a plurality of particles is prepared, and wherein in (i), the sol is added as a spray of droplets.

6. A process according to claim 5, wherein the droplets have a diameter from 5 micron to 5 mm.

7. A process according to claim 5, wherein the spray of droplets is produced by a vibrating accoustically modulated nozzle.

8. A process according to claim 7, wherein the spray of droplets is deflected electrostatic charging.

9. A process according to claim 1, wherein the sol is destabilised prior to freezing.

10. A process according to claim 1 wherein, in (ii), the temperature of the solid, quenched sol is raised at a rate from 1000° C./min to 0.2° C./min.

11. A process accoding to claim 1, wherein the or each porous oxide or hydroxide body is heated at a temperature above ambient.

12. A process for the preparation of at least one porous oxide or hydroxide body having a uniformly distributed network of macropores having a diameter greater than 500 nm interconnected with micropores having a diameter of 1 to 10 nm, which process comprises:

(i) adding at least one body consisting essentially of a sol of the oxide or hydroxide to a fluid freezing medium to thereby obtain a solid, quenched sol;

(ii) recovering said solid quenched sol and raising its temperature so that solvent nucleation occurs in at least step (ii), resulting in the formation of crystals of the dispersion medium and the dispersion medium melts, and (iii) separating one or more solid porous bodies having a uniformly distributed network of macropores having a diameter greater than 500 nm interconnected with micropores having a diameter of 1 to 10 nm from the dispersant.

13. A porous oxide or hydroxide body having a pores of a diameter greater than 500 nm prepared by a process comprising:

(i) adding at least one body consisting essentially of a sol of the oxide or hydroxide to a fluid freezing medium to thereby obtain a solid, quenched sol;

(ii) recovering said solid quenched sol and raising its temperature so that solvent nucleation occurs in at least step (ii), resulting in the formation of crystals of the dispersion medium and the dispersion medium melts, and (iii) separating one or more solid porous bodies having pores of a diameter greater than 500 nm from the dispersant.

14. A porous body, or porous particles, according to claim 13, wherein the oxide comprises silica.

15. A porous body, or porous particles, according to claim 13, having a porosity greater than 1 ml/g.

16. A porous body, or porous oxide particles, according to claim 13, having pore diameters in the range of 1,000 to 10,000 nm.

17. A porous body, or porous oxide particles, according to claim 13, having an average particle size not greater than 5 mm.

18. A porous oxide or hydroxide body having a uniformly distributed network of macropores of a diameter greater than 500 nm interconnected with micropores having a diameter of 1 to 10 nm prepared by a process comprising:

(i) adding at least one body consisting essentially of a sol of the oxide or hydroxide to a fluid freezing medium to thereby obtain a solid, quenched sol;

(ii) recovering said solid quenched sol and raising its temperature so that solvent nucleation occurs in at least step (ii), resulting in the formation of crystals of the dispersion medium and the dispersion medium melts; and (iii) separating one or more solid porous bodies having a uniformly distributed network of macropores of a diameter greater than 500 nm interconnected with micropores having a diameter of 1 to 10 nm from the dispersant.

* * * * *